(12) United States Patent
Kosover et al.

(10) Patent No.: US 7,691,952 B2
(45) Date of Patent: *Apr. 6, 2010

(54) SULFONATED NITROPHENOLS AS POLYMERIZATION INHIBITORS

(75) Inventors: Vilan Kosover, Cheshire, CT (US); Jesus A. Fabian, Wethersfield, CT (US); Istvan Lippai, Naugatuck, CT (US); Brigitte Benage, Wolcott, CT (US); Gerald J. Abruscato, Southington, CT (US)

(73) Assignee: Chemtura Corporation, Middlebury, CT (US)

( * ) Notice: Subject to any disclaimer, the term of this patent is extended or adjusted under 35 U.S.C. 154(b) by 40 days.

This patent is subject to a terminal disclaimer.

(21) Appl. No.: 11/172,168

(22) Filed: Jun. 29, 2005

(65) Prior Publication Data

US 2006/0069218 A1 Mar. 30, 2006

Related U.S. Application Data

(60) Provisional application No. 60/614,377, filed on Sep. 28, 2004, provisional application No. 60/632,529, filed on Dec. 3, 2004.

(51) Int. Cl.
 *C08F 2/38* (2006.01)
 *C08K 3/00* (2006.01)
(52) U.S. Cl. .............................. 526/82; 526/83; 526/84; 252/182.29
(58) Field of Classification Search .................. 526/82, 526/83, 84; 252/182.29
See application file for complete search history.

(56) References Cited

U.S. PATENT DOCUMENTS

| | | | |
|---|---|---|---|
| 2,046,356 A | 7/1936 | Wyler et al. ..................... 260/69 |
| 2,867,672 A | 1/1959 | Hemmerich ............. 260/666.5 |
| 3,163,677 A | 12/1964 | Hoffmann et al. ........... 260/583 |
| 3,334,103 A | 8/1967 | Feldman et al. ............. 260/290 |
| 3,372,182 A | 3/1968 | Hoffmann et al. ........ 260/465.5 |
| 3,422,144 A | 1/1969 | Hoffmann et al. ........... 260/570 |
| 3,494,930 A | 2/1970 | Dupeyre et al. .......... 260/294.7 |
| 3,502,692 A | 3/1970 | Feldman et al. .......... 260/326.3 |
| 3,873,564 A | 3/1975 | Schneider et al. ........ 260/309.6 |
| 3,966,711 A | 6/1976 | Rasberger ................. 260/239.3 |
| 4,086,147 A | 4/1978 | Watson .......................... 203/9 |
| 4,451,374 A | 5/1984 | Peterson et al. |
| 4,468,343 A | 8/1984 | Butler et al. ................. 252/403 |
| 4,665,185 A | 5/1987 | Winter et al. ................ 546/184 |
| 4,670,131 A | 6/1987 | Ferrell .......................... 208/48 |
| 5,254,760 A | 10/1993 | Winter et al. .................... 585/5 |
| 5,290,888 A | 3/1994 | Gatechair et al. ............. 526/83 |
| 5,446,220 A | 8/1995 | Arhancet ........................ 585/5 |
| 5,545,782 A | 8/1996 | Winter et al. .................... 585/5 |
| 5,545,786 A | 8/1996 | Winter et al. ................ 585/435 |
| 5,932,735 A | 8/1999 | Cunkle et al. ............... 546/242 |
| 6,143,205 A | 11/2000 | Sutoris et al. ............... 252/405 |
| 6,403,850 B1 * | 6/2002 | Benage et al. .................. 585/5 |
| 2003/0194523 A1 * | 10/2003 | Kume et al. ................ 428/40.1 |
| 2004/0147797 A1 | 7/2004 | Tanizaki et al. ............. 585/950 |
| 2006/0122341 A1 * | 6/2006 | Kosover et al. ............... 526/82 |

FOREIGN PATENT DOCUMENTS

| | | |
|---|---|---|
| EP | 0765856 A1 | 4/1997 |
| GB | 2171926 | 9/1986 |
| JP | 06234700 * | 8/1994 |
| JP | 06234700 A * | 8/1994 |
| SU | 1027150 | 7/1983 |
| SU | 1139722 | 2/1985 |
| SU | 1558888 | 4/1990 |
| WO | 98/25872 | 6/1998 |

* cited by examiner

*Primary Examiner*—William K Cheung
(74) *Attorney, Agent, or Firm*—Katten Muchin Rosenman LLP

(57) ABSTRACT

Disclosed herein is a method for inhibiting and retarding the premature polymerization and the polymer growth of ethylenically unsaturated monomers comprising adding to said monomers an effective amount of at least one inhibitor that is a sulfonated nitrophenol of the formula:

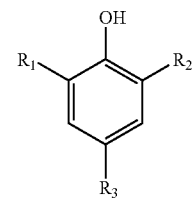

wherein:

$R_1$, $R_2$, and $R_3$ are independently selected from the group consisting of hydrogen, alkyl, $NO_2$, and $SO_3H$, provided that at least one of $R_1$, $R_2$, and $R_3$ is $NO_2$ and at least one of $R_1$, $R_2$, and $R_3$ is $SO_3H$. In a preferred embodiment, at least one additional inhibitor selected from the group consisting of nitroxyl compounds, nitrosoanilines, nitrophenols, amines, and mixtures thereof is also added.

18 Claims, No Drawings

SULFONATED NITROPHENOLS AS POLYMERIZATION INHIBITORS

We claim the benefit under Title 35, United States Code, §120 of U.S. Provisional Application No. 60/614,377, filed Sep. 28, 2004, entitled SULFONATED NITROPHENOLS POLYMERIZATION INHIBITORS and Provisional Application No. 60/632,529, filed Dec. 3, 2004, entitled SULFONATED NITROPHENOL AS POLYMERIZATION INHIBITORS.

BACKGROUND OF THE INVENTION

1. Field of the Invention

The present invention is directed to the inhibition and retardation of polymerization of ethylenically unsaturated monomers by means of the addition thereto of a sulfonated nitrophenol.

2. Description of Related Art

Many ethylenically unsaturated monomers undesirably polymerize at various stages of their manufacture, processing, handling, storage, and use. Polymerization, such as thermal polymerization, during their purification results in the loss of the monomer, i.e., a lower yield, and an increase in the viscosity of any tars that may be produced. The processing and handling of the higher viscosity tars then require higher temperature and work (energy cost) to remove residual monomer.

Polymerization can also result in equipment fouling, especially in the case of production of acrylic monomers. Such polymerization causes loss in production efficiency owing to the deposition of polymer in or on the equipment being used. These deposits must be removed from time to time, leading to additional loss in production of the monomer.

A wide variety of compounds has been proposed and used for inhibiting uncontrolled and undesired polymerization of ethylenically unsaturated monomers. However, many of these compounds have not been fully satisfactory.

U.S. Pat. No. 2,867,672 discloses that the polymerization of uninhibited styrene condensing in liquid form on the surfaces containing the vapor space above the liquid level of the main body of styrene in a tank may be minimized by spraying the surfaces enclosing the vapor space with a styrene polymerization inhibitor.

U.S. Pat. No. 4,086,147 discloses a process for the distillation of readily polymerizable vinyl aromatic compounds comprising subjecting a vinyl aromatic compound to elevated temperatures in a distillation system in the presence of a polymerization inhibitor comprising m-nitro-p-cresol.

U.S. Pat. No. 4,468,343 discloses a compound and a process for utilizing the compound to prevent the polymerization of vinyl aromatic compounds, such as styrene, during heating. The composition includes effective amounts of 2,6-dinitro-p-cresol and either a phenylenediamine or 4-tert-butylcatechol respectively, to act as a polymerization co-inhibitor system in the presence of oxygen.

U.S. Pat. No. 4,670,131 discloses controlling the fouling of equipment used for processing of organic feed streams containing olefinic compounds by inhibiting polymerization of the olefinic compounds by carrying out the processing in the presence of from about 20 ppb to less than 1000 ppb of a stable free radical, such as a nitroxide.

U.S. Pat. No. 5,254,760 discloses the inhibition of the polymerization of a vinyl aromatic compound, such as styrene, during distillation or purification by the presence of at least one stable nitroxyl compound together with at least one aromatic nitro compound.

U.S. Pat. No. 5,290,888 discloses a process for stabilizing an ethylenically unsaturated monomer or oligomer from premature polymerization whereby a stabilizing amount of an N-hydroxy substituted hindered amine is added to said polymerizable monomer or oligomer. The ethylenically unsaturated monomer or oligomer encompass vinyl monomers or oligomers bearing at least one polymerizable moiety. The N-hydroxy substituted hindered amine is said to inhibit premature polymerization in the liquid and/or vapor phase.

U.S. Pat. No. 5,446,220 discloses methods for inhibiting the polymerization of vinyl aromatic monomers in oxygen-free processing systems. These methods comprise adding from 1 to about 10,000 parts per million parts monomer of a combination of a dinitrophenol compound, a hydroxylamine compound and a phenylenediamine compound. Preferably, 2-sec-butyl-4,6-dinitrophenol or 4,6-dinitro-o-cresol are used in combination with bis-(hydroxypropyl)hydroxylamine and N,N'-di-sec-butyl-p-phenylenediamine.

U.S. Pat. No. 5,545,786 discloses that nitroxyl inhibitors in combination with some oxygen reduce the premature polymerization of vinyl aromatic monomers during the manufacturing processes for such monomers. It is also disclosed that even small quantities of air used in combination with the nitroxyl inhibitors result in vastly prolonged inhibition times for said monomers.

U.S. Pat. No. 5,932,735 discloses that selected derivatives of 1-oxyl-2,2,6,6-tetramethyl-4-hydroxypiperidine are effective as inhibitors to prevent the premature polymerization of acrylic and methacrylic acids, their esters, their amides, vinyl acetate and acrylonitrile in the presence of water.

U.S. Pat. No. 6,143,205 discloses a mixture for inhibiting the premature polymerization of monomers that contains (A) vinyl-containing monomers, and (B) an effective amount of a mixture of (i) from 0.05 to 4.5% by weight, based on the total mixture (B), of at least one N-oxyl compound of a secondary amine which carries no hydrogen atoms on the α-carbon atoms and (ii) from 99.95 to 95.5% by weight, based on the total mixture (B), of at least one nitro compound.

Russian patents 1,027,150; 1,139,722; and 1,558,888 disclose decreased polymer formation during normal operating conditions (true inhibitors), but do not protect the system in emergency feed shut off situations, i.e., there is no retarder effect.

The foregoing are incorporated herein by reference in their entirety.

SUMMARY OF THE INVENTION

In accordance with the present invention, sulfonated nitrophenols have been found to be excellent inhibitors and retarders to prevent polymerization of ethylenically unsaturated compounds. Optionally, these materials can be used in combination with nitrophenols, such as 2,4-dinitro-o-sec-butylphenol (DNBP); nitroxyl radical type compounds, such as 4-oxo-TEMPO with nitrophenols and amines, such as N-methyl-pyrrolidinone (NMP); nitrosoanilines, e.g., C-nitrosoanilines, such as 4-nitroso-N-(1,4-dimethylpentyl)-aniline with nitrophenols and amines; and the like; and combinations of the foregoing.

It is an advantage of the present invention that the sulfonated nitrophenols can be easily prepared in nitrophenol production by changing the nitration conditions.

It is thus an object of the present invention to develop a highly efficient and inexpensive polymerization inhibitor with superb true inhibitor and retarder capabilities.

This and other objects are obtained by the present invention, which is directed to a method for inhibiting and retarding the premature polymerization and the polymer growth of ethylenically unsaturated monomers comprising adding to said monomers an effective amount of at least one inhibitor that is a sulfonated nitrophenol of the formula:

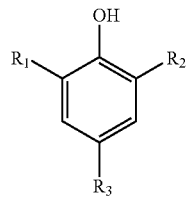

wherein:

$R_1$, $R_2$, and $R_3$ are independently selected from the group consisting of hydrogen, hydrocarbyl, $NO_2$, and $SO_3H$, provided that at least one of $R_1$, $R_2$, and $R_3$ is $NO_2$ and at least one of $R_1$, $R_2$, and $R_3$ is $SO_3H$.

In a preferred embodiment, the present invention is directed to a method for inhibiting and retarding the premature polymerization and the polymer growth of ethylenically unsaturated monomers comprising adding to said monomers an effective amount of a combination of (A) at least one first inhibitor that is a sulfonated nitrophenol of the formula:

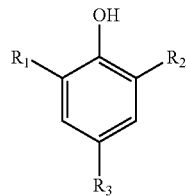

wherein:

$R_1$, $R_2$, and $R_3$ are independently selected from the group consisting of hydrogen, hydrocarbyl, $NO_2$, and $SO_3H$, provided that at least one of $R_1$, $R_2$, and $R_3$ is $NO_2$ and at least one of $R_1$, $R_2$, and $R_3$ is $SO_3H$; and (B) at least one second inhibitor selected from the group consisting of nitroxyl compounds, nitrosoanilines, nitrophenols, amines, and mixtures thereof

DESCRIPTION OF THE PREFERRED EMBODIMENTS

As stated above, the present invention is directed to inhibitors comprising a method for inhibiting and retarding the premature polymerization and the polymer growth of ethylenically unsaturated monomers comprising adding to said monomers an effective amount of at least one inhibitor that is a sulfonated nitrophenol of the formula:

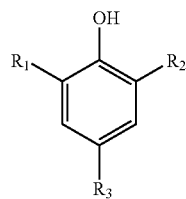

wherein:

$R_1$, $R_2$, and $R_3$ are independently selected from the group consisting of hydrogen, hydrocarbyl, $NO_2$, and $SO_3H$, provided that at least one of $R_1$, $R_2$, and $R_3$ is $NO_2$ and at least one of $R_1$, $R_2$, and $R_3$ is $SO_3H$.

The sulfonated nitrophenols employed in the practice of the present invention can be easily produced in a two step process. The phenol starting material is treated with concentrated $H_2SO_4$ to yield a sulfonated phenol intermediate. The sulfonated phenol is then reacted with $HNO_3$. The $HNO_3$:phenol molar ratio should be from about 0.5 to about 1.9, preferably from about 0.9 to about 1.1. The concentration of nitric acid should be from about 1 to about 65%, preferably from about 16 to about 35%. The temperature should be in the range of from about 40 to about 80° C. The end product may contain some nitrophenol, which also has good retarder activity.

In a preferred embodiment the inhibiting system further comprises one or more additional inhibitors selected from the group consisting of nitrophenols, nitroxyl compounds, nitrosoanilines, amines, and mixtures thereof.

Where one of $R_1$, $R_2$, and $R_3$ is hydrocarbyl, it is preferably a straight chain or branched chain alkyl or alkenyl of from 1 to 18 carbon atoms, more preferably of from 1 to 12 carbon atoms including, but not limited to, methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, oleyl, isomers of the foregoing, such as isopropyl, sec-butyl, neopentyl, and the like; or cyclic alkyl groups, such as cyclopentyl, cyclohexyl, cycloheptyl, cyclooctyl, and cyclododecyl.

Nitrophenols that can be employed in the practice of the present invention include, but are not limited to, 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 4-cyano-2-nitrophenol, 3-iodo-4-cyano-5-nitrophenol, m-nitro-p-cresol, 2,6-dinitro-p-cresol, and the like. 2,4-Dinitro-6-sec-butylphenol is preferred.

The sulfonated nitrophenols of the present invention can also be advantageously employed with an additional inhibitor that is a nitroxyl compound, preferably a stable hindered nitroxyl compound having the structural formula:

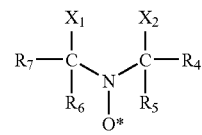

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl; and $X_1$ and $X_2$ (1) are independently selected from the group consisting of halogen, cyano, $COOR_{10}$, —S—$COR_{10}$, —$OCOR_{10}$, (wherein $R_{10}$ is alkyl or aryl), amido, —S—$C_6H_5$, carbonyl, alkenyl, or alkyl of 1 to 15 carbon atoms, or (2) taken together, form a ring structure with the nitrogen.

In a particularly preferred embodiment, the stable hindered nitroxyl compound has the structural formula:

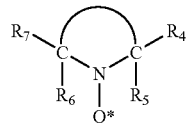

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl, and the

portion represents the atoms necessary to form a five-, six-, or seven-membered heterocyclic ring.

Accordingly, one of the several classes of cyclic nitroxides that can be employed in the practice of the present invention can be represented by the following structural formula:

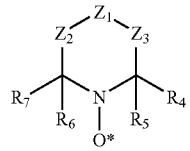

wherein $Z_1$, $Z_2$ and $Z_3$ are independently selected from the group consisting of oxygen, sulfur, secondary amines, tertiary amines, phosphorus of various oxidation states, and substituted or unsubstituted carbon atoms, such as >$CH_2$, >$CHCH_3$, >$C=O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CR_8OR_9$, >$CHNR_8R_9$, >$CCONR_8R_9$, >$C=NOH$, >$C=CH\text{-}C_6H_5$, >$CF_2$, >$CCl_2$, >$CBr_2$, >$CI_2$, >$CR_8PR_{13}R_{14}R_{15}$, and the like, where $R_8$ and $R_9$ are independently selected from the group consisting of hydrogen, alkyl, aryl, and acyl and $R_{13}$, $R_{14}$, and $R_{15}$ are independently selected from the group consisting of unshared electrons, alkyl, aryl, =O, $OR_{16}$, and $NR_{17}R_{18}$, where $R_{16}$, $R_{17}$, and $R_{18}$ are independently selected from the group consisting of hydrogen, alkyl, and aryl. Where $R_8$ and/or $R_9$ are alkyl, it is preferred that they be a lower alkyl (i.e., one having one to five carbon atoms, e.g., methyl, ethyl, propyl, butyl, pentyl, and isomers thereof).

Where $R_8$ and/or $R_9$ are aryl, it is preferred that they be aryl of from 6 to 10 carbon atoms, e.g., phenyl or naphthyl, which, in addition, may be substituted with non-interfering substituents, e.g., lower alkyl groups, halogens, and the like.

Where $R_8$ and/or $R_9$ are acyl, it is preferred that they be acyl of the structure

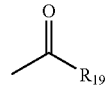

where $R_{19}$ is alkyl, aryl, $OR_{20}$, or $NR_{20}R_{21}$ and where $R_{20}$ and $R_{21}$, are alkyl, aryl, or

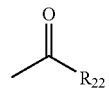

where $R_{22}$ is alkyl or aryl. Where $R_{19}$, $R_{20}$, $R_{21}$, or $R_{22}$ are alkyl, they are preferably alkyl of from 1 to 15 carbon atoms, more preferably lower alkyl of from 1 to 5 carbon atoms, as described above. Where $R_{19}$, $R_{20}$, $R_{21}$, or $R_{22}$ are aryl, they are preferably aryl of from 6 to 10 carbon atoms, as described above.

Another of the several classes of cyclic nitroxides that can be employed in the practice of the present invention can be represented by the following structural formula:

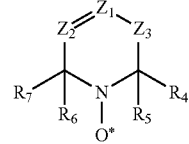

wherein $Z_1$ and $Z_2$, which may be the same or different, are nitrogen or substituted or unsubstituted carbon atoms, such as =$C(H)$—, =$C(CH_3)$—, =$C(COOH)$—, =$C(COOCH_3)$—, =$C(COOC_2H_5)$—, =$C(OH)$—, =$C(CN)$—, =$C(NR_8R_9)$—, =$C(CONR_8R_9)$—, and the like, and where $Z_3$, $R_8$, and $R_9$ are as described above.

The cyclic nitroxides employed in the practice of the present invention can also be derived from five-membered rings. These compounds are of the structure:

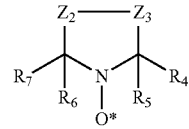

wherein $Z_2$ and $Z_3$, which may be the same or different, are sulfur, oxygen, secondary amines, tertiary amines, phosphorus of various oxidation states, or substituted or unsubstituted carbon atoms, such as, >$CH_2$, >$CHCH_3$, >$C=O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CR_8OR_9$, >$CHNR_8R_9$, >$CCONR_8R_9$, >$C=NOH$, >$C=CH$—$C_6H_5$, $CF_2$, >$CCl_2$, $CBr_2$, $CI_2$, >$CR_8PR_{13}R_{14}R_{15}$, and the like, wherein the several R groups are as described above.

The cyclic nitroxides employed in the practice of the present invention can also have the structure:

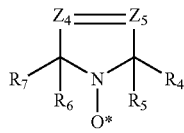

wherein $Z_4$ and $Z_5$, which can be the same or different, can be nitrogen or a substituted or unsubstituted carbon atom, such as =C(H)—, =C(CH$_3$)—, =C(COOH)—, =C(COOCH$_3$)—, =C(COOC$_2$H$_5$)—, =C(OH)—, =C(CN)—, =C(NR$_8$R$_9$)—, =C(CONR$_8$R$_9$)—, and the like, where $R_8$ and $R_9$ are as described above.

Another class of cyclic nitroxides that can be employed in the practice of the present invention is of the structure:

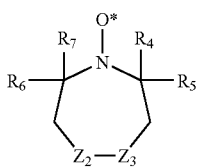

wherein $Z_2$ and $Z_3$, which may be the same or different, are sulfur, oxygen, secondary amines, tertiary amines, or substituted or unsubstituted carbon atoms, such as, >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CHNR$_8$R, >CCONR$_8$R$_9$, >CR$_8$OR$_9$, >C=NOH, >C=CH—C$_6$H$_5$, CF$_2$, CCl$_2$, CBr$_2$, C$_{12}$, >CR$_8$PR$_{13}$R$_{14}$R$_{15}$, and the like, where the several R groups are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, for all the nitroxyl structures above, $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl. The alkyl (or heteroatom-substituted alkyl) groups $R_4$ through $R_7$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that $R_4$ through $R_7$ be independently selected lower alkyl (or heteroatom-substituted lower alkyl) of one to five carbon atoms (e.g., methyl, ethyl, propyl, butyl, pentyl, and isomers thereof). Where heteroatom substituents are present, they can, for example, include halogen, oxygen, sulfur, nitrogen, and the like. It is most preferred that all of $R_4$ through $R_7$ be methyl.

Examples of suitable nitroxide free radical compounds that can be used in combination with the sulfonated nitrophenols in the practice of the present invention, include, but are not limited to:
N,N-di-tert-butylnitroxide;
N,N-di-tert-amylnitroxide;
N-tert-butyl-2-methyl-1-phenyl-propylnitroxide;
N-tert-butyl-1-diethylphosphono-2,2-dimethylpropylnitroxide;
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)n-butylmalonate;
bis(1-oxyl-2,2,6,6-tetramethylpiperidin-4-yl)phthalate;
bis(1-oxyl-2,2,6,6-tetramethylpiperidin-4-yl)isophthalate;

bis(1-oxyl-2,2,6,6-tetramethylpiperidin-4-yl)terephthalate;
bis(1-oxyl-2,2,6,6-tetramethylpiperidin-4-yl)hexahydroterephthalate;
N,N'-bis(1-oxyl-2,2,6,6-tetramethylpiperidin-4-yl)adipamide;
N-(1-oxyl-2,2,6,6-tetramethylpiperidin-4-yl)caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine;
4,4'-ethylenebis(1-oxyl-2,2,6,6-tetramethylpiperazin-3-one); and the like.

As used herein, the abbreviation TEMPO stands for 2,2,6,6-tetramethyl-1-piperidinyloxy. Thus, 4-amino-TEMPO is 4-amino-2,2,6,6-tetramethyl-1-piperidinyloxy; 4-hydroxy-TEMPO is 4-hydroxy-2,2,6,6-tetramethyl-1-piperidinyloxy (also known in the art as HTEMPO); 4-oxo-TEMPO is 4-oxo-2,2,6,6-tetramethyl-1-piperidinyloxy; and so on.

It is preferred that one member of a combination employed in the practice of the present invention be 4-amino-TEMPO, 4-oxo-TEMPO, 4-hydroxy-TEMPO, or TEMPO.

Blends of two or more of the foregoing, e.g., 4-amino-TEMPO and 4-oxo-TEMPO, can also be employed.

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.) They are suitable for use over a wide range of temperatures, but distillation temperatures employed with the ethylenically unsaturated monomers that are stabilized by the process of the present invention typically range from about 60° C. to about 180° C., preferably from about 70° C. to about 165° C., and, more preferably, from about 80° C. to about 150° C. Such distillations are generally performed at an absolute pressure in the range of about 10 to about 1,200 mm of Hg.

Where an inhibiting system of the present invention comprises an additional inhibitor that is a nitrosoaniline, it can be an N-nitrosoaniline or a C-nitrosoaniline. Preferably, the nitrosoaniline compound is a C-nitrosoaniline.

C-nitrosoaniline compounds can be prepared by C-nitrosation of the corresponding anilines in any typical manner used for the C-nitrosation of aromatic amines. For example, reaction of the amine with cold nitrous acid produces an N-nitroso compound that rearranges to a para-nitrosoaniline under the influence of an excess of hydrochloric acid. In some cases, it is more convenient to effect the nitrosation and rearrangement in one step by conducting the reaction in methanol solution in the presence of an excess of hydrogen chloride under anhydrous conditions. This procedure is described in U.S. Pat. No. 2,046,356.

Those skilled in the art will be aware that nitrosoaniline derivatives are understood to tautomerize to quinone imine oxime derivatives, i.e.,

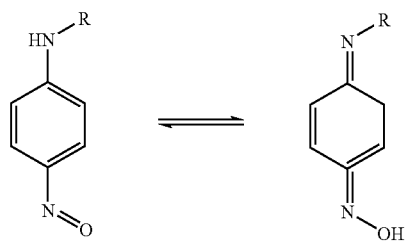

See, for example, Sidgwick, N. V., *The Organic Chemistry of Nitrogen*, Third Edition, Clarendon Press, Oxford, 1966. Thus, both forms can be present, especially in solution at elevated temperatures, and can be expected to contribute to the inhibiting activity of these compounds.

Where the inhibiting system of the present invention comprises a C-nitrosoaniline, it is preferably one having the structure:

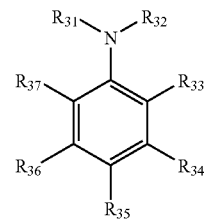

wherein $R_{31}$ and $R_{32}$ are independently selected from the group consisting of hydrogen, alkyl, aryl, acyl, hydroxyl, alkoxy, nitroso, and sulfonyl, or $R_{31}$ and $R_{32}$ can form a cyclic ring that is aryl, cycloalkyl, polyaryl, or heterocyclic;

$R_{33}$ through $R_{37}$ are independently selected from the group consisting of hydrogen, alkyl, aryl, acyl, hydroxyl, alkoxy, acyloxy, $NR_8(R_{39})$, nitro, nitroso, halogen, and sulfonyl, or any two adjacent R's can form a cyclic ring that is aryl, cycloalkyl, polyaryl, or heterocyclic, provided that at least one of $R_{33}$ through $R_{37}$ must be a nitroso group; and $R_{38}$ and $R_{39}$ are independently selected from the group consisting of hydrogen, alkyl, aryl, acyl, and nitroso. Preferably $R_{38}$ is hydrogen and $R_{39}$ is alkyl.

Where the inhibiting system of the present invention comprises an additional inhibitor that is an amine, the amine can be primary, secondary, or tertiary amine, and can comprise alkyl groups, aryl groups, or combinations thereof. Such amines include, but are not limited to, α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-β-naphthylamine, isopropoxydiphenylamine, aldol-α-naphthyl amine, symmetrical di-β-naphthyl-p-phenylenediamine, trimethyl dihydroquinoline, ditolylamines, phenyl-α-naphthylamine, phenyl-β-naphthylamine, diaminophenol, 4-cyclohexylaminophenol, p-aminophenol, o-aminophenol, 5-amino-2-hydroxytoluene, and the like.

The ethylenically unsaturated monomer, the premature polymerization and polymer growth of which is an object of the present invention, can be any such monomer for which unintended polymerization and/or polymer growth during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, isoprene, and the like.

The ethylenically unsaturated monomers will not necessarily be stabilized indefinitely by the presence of the inhibitor(s), especially when the monomers are heated as in distillation, but they can be considered to be stabilized as long as A) there is a measurable increase in the time for which they can be heated before the onset of polymerization and/or polymer growth in a static system, B) the amount of polymer made at a constant temperature remains constant over time in a dynamic system, and/or C) the rate of polymer growth is significantly slower than when the growth inhibiting system is not present.

Those skilled in the art will understand that, if desired, free radical scavengers can also be included in the practice of the present invention. For example, air or $O_2$, as disclosed in U.S. Pat. Nos. 5,545,782 and 5,545,786, can be added, as can the aromatic nitro compounds disclosed in U.S. Pat. No. 5,254,760, the dihetero-substituted benzene compounds having at least one transferable hydrogen, e.g., a quinone derivative such as the mono-methyl-ether of hydroquinone disclosed in European Pat. Application 0 765 856 A1, the iron compounds disclosed in WO 98/25872, and other inhibitors, e.g., phenolics and certain inorganic salts, well-known to those skilled in the art.

The polymerization inhibitors can be introduced into the monomer to be protected by any conventional method. They can, for example, be added as a concentrated solution in suitable solvents just upstream from the point of desired application by any suitable means. In addition, individual inhibiting components can be injected separately into the distillation train along with the incoming feed and/or through separate and multiple entry points, provided there is an efficient distribution of the inhibiting composition. Since the inhibitors are gradually depleted during the distillation operation, it is generally advantageous to maintain the appropriate amount of them in the distillation apparatus by adding them during the course of the distillation process. Adding inhibitors can be done either on a generally continuous basis or intermittently, in order to maintain the inhibitor concentration above the minimum required level.

The total inhibitor concentration should be from about 1 to about 2000 ppm versus the monomer being inhibited; preferably from about 5 to about 1000 ppm, depending on the conditions of use. The amine is preferably present in a range of from about 1 to about 500 ppm, more preferably from about 1 to about 300 ppm; the nitroxy radical type compound is preferably present in a range of from about 1 to about 1000 ppm, more preferably from about 5 to about 500 ppm; the nitrosoaniline is preferably present in a range of from about 1 to about 1000 ppm, more preferably from about 5 to about 500 ppm; and the nitrophenol is preferably present in a range of from about 1 to about 1000 ppm, more preferably from about 5 to about 500 ppm.

The advantages and the important features of the present invention will be more apparent from the following examples.

EXAMPLES

Example 1

A quantity of 471 grams of a 17% $HNO_3$ solution was placed in a round bottomed flask, equipped with an overhead stirrer, thermometer, addition funnel, and reflux condenser, and heated to 80° C. To this acid, a portion (162 grams) of sulfonated o-sec-butylphenol, made by the sulfonation of 300 grams of o-sec-butylphenol (OSBP) with 280 grams concentrated $H_2SO_4$ at 84° C., was added. The addition was subsurface and dropwise. The separation of reaction mixture resulted in two layers. The upper (aqueous acid) layer (509 grams) was separated from the lower (2,4-dinitro-o-sec-butylphenol) layer (104.6 grams) and 464 grams was evaporated in a 2 mm Hg vacuum at a temperature not exceeding 30° C. for 75 minutes. This residue (173 grams) was transferred into a separatory funnel. Recovery of the upper (organic) layer resulted in 37.1 grams of a mixture containing 4-hydroxy-5-sec-butyl-3-nitrobenzenesulfonic acid and 2-hydroxy-3-sec-butyl-5-nitrobenzenesulfonic acid.

The styrene inhibitor and retarder properties of this material were tested in a continuous dynamic reboiler test monitoring the polymer formation with UV spectrophotometry at a 500 ppm inhibitor concentration. According to this test, the inhibitor is added to styrene monomer from which tert-butyl-catechol (TBC) has been previously removed by distillation. This styrene (180 grams) is loaded into a flask which is immersed into an oil bath. The temperature of the styrene is usually 116° C. During the test, a fresh feed is charged into the flask at the rate of three grams/minute and, at the same time, the material from the flask is discharged at the same rate. The steady stage is continued until equilibrium. For the feed shut off stage, the charging and discharging are discontinued. Samples are taken every hour at the steady stage and every 5-10 minutes at feed shut off.

After 5 hours of steady stage, 0.0005% polymer was measured, while 1 hour feed shut off resulted in 0.03% polymer.

Example 2

A mixture of 4-hydroxy-5-sec-butyl-3-nitrobenzenesulfonic acid and 2-hydroxy-3-sec-butyl-5-nitrobenzenesulfonic acid, produced at plant scale, was tested in the procedure described in Example 1 at a concentration of 500 ppm. This material also contained 21% of dinitro sec.-butyl phenol (DNBP). During the steady stage test, 0.0004% polymer was formed, while the shut off test resulted in 0.038% polymer after one hour.

As a comparison, when DNBP was tested alone using the same procedure, the steady state polymer formation was 0.11% while the 1 hour feed shut off revealed 1.18% polymer.

Example 3

Three hundred grams of OSBP was sulfonated with 280 grams of 98% sulfuric acid as described in Example 1. Two hundred grams of this material was used for nitration with an $HNO_3$:OSBP molar ratio of 1.6:1 using the following procedure.

Nitric acid (35%; 171.4 grams) was charged into a round bottomed flask and to it the 200 grams of sulfonated OSBP was added dropwise in two hours at 40° C. The mixture was then transferred into a separatory funnel where two layers were formed. The 151 grams of bottom layer was identified as 40% sulfuric acid while the top (organic) phase was recovered as a 1:1 blend of DNBP and mixture of 4-hydroxy-5-sec-butyl-3-nitrobenzenesulfonic acid and 2-hydroxy-3-sec-butyl-5-nitrobenzenesulfonic acid.

Example 4

The mixture of 4-hydroxy-5-sec-butyl-3-nitrobenzenesulfonic acid and 2-hydroxy-3-sec-butyl-5-nitrobenzenesulfonic acid (250 ppm) of Example 3 was tested in the presence of 4-oxo-TEMPO/NMP/DNBP (100 ppm/90 ppm/250 ppm). Five hours steady stage resulted in 0.0005% of polymer, while 2 hours feed shut off generated 0.101% polymer.

Example 5

The mixture of 4-hydroxy-5-sec-butyl-3-nitrobenzenesulfonic acid and 2-hydroxy-3-sec-butyl-5-nitrobenzenesulfonic acid (250 ppm) of Example 3 was tested in the presence of 4-nitroso-N-(2,4-dimethylpentyl)-aniline/NMP/

DNBP (100 ppm/90 ppm/250 ppm). Five hours steady stage resulted in 0.002% polymer, while 2 hrs feed shut off generated 0.0057% polymer.

In view of the many changes and modifications that can be made without departing from principles underlying the invention, reference should be made to the appended claims for an understanding of the scope of the protection to be afforded the invention.

What is claimed is:

1. A method for inhibiting and retarding the premature polymerization and the polymer growth of styrene monomer comprising adding to said styrene monomer an effective amount of at least one inhibitor that is a sulfonated nitrophenol of the formula:

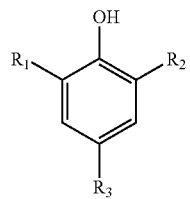

wherein:

$R_1$, $R_2$, and $R_3$ are independently selected from the group consisting of hydrocarbyl, $NO_2$ and $SO_3H$, provided that one of $R_1$, $R_2$, and $R_3$ is $NO_2$, one of $R_1$, $R_2$, and $R_3$ is hydrocarbyl, and one of $R_1$, $R_2$, and $R_3$ is $SO_3H$; and the total inhibitor concentration is in the range of from about 1 to about 2000 ppm versus the styrene monomer being inhibited.

2. The method of claim 1 wherein the hydrocarbyl is a straight chain or branched chain alkyl or alkenyl of from 1 to 18 carbon atoms.

3. The method of claim 2 wherein the hydrocarbyl is selected from the group consisting of methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, oleyl, isomers of the foregoing, cyclopentyl, cyclohexyl, cycloheptyl, cyclooctyl, and cyclododecyl.

4. A method for inhibiting and retarding the premature polymerization and the polymer growth of styrene monomer comprising adding to said styrene monomer an effective amount of a combination of (A) at least one first inhibitor that is a sulfonated nitrophenol of the formula:

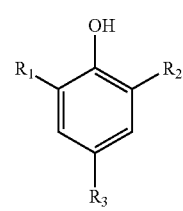

wherein:

$R_1$, $R_2$, and $R_3$ are independently selected from the group consisting of hydrocarbyl, $NO_2$ and $SO_3H$, provided that one of $R_1$, $R_2$, and $R_3$ is $NO_2$, one of $R_1$, $R_2$, and $R_3$ is hydrocarbyl, and one of $R_1$, $R_2$, and $R_3$ is $SO_3H$;

(B) at least one second inhibitor selected from the group consisting of nitroxyl compounds, nitrosoanilines, nitrophenols, amines, and mixtures thereof;

wherein the total inhibitor concentration is in the range of from about 1 to about 2000 ppm versus the styrene monomer being inhibited.

5. The method of claim 4 wherein the hydrocarbyl is a straight chain or branched chain alkyl or alkenyl of from 1 to 18 carbon atoms.

6. The method of claim 5 wherein the hydrocarbyl is selected from the group consisting of methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, oleyl, isomers of the foregoing, cyclopentyl, cyclohexyl, cycloheptyl, cyclooctyl, and cyclododecyl.

7. The method of claim 4 wherein the second inhibitor comprises a mixture of 1 to 1000 ppm of at least one nitroxyl compound, 1-500 ppm of at least one amine, and 1 to 1000 ppm of at least one nitrophenol.

8. The method of claim 4 wherein the second inhibitor comprises a mixture of 1 to 1000 ppm of at least one nitrosoaniline, 1-500 ppm of at least one amine, and 1 to 1000 ppm of at least one nitrophenol.

9. A method for inhibiting and retarding the premature polymerization and the polymer growth of styrene monomer comprising adding to said styrene monomer an effective amount of at least one inhibitor that is a sulfonated nitrophenol selected from the group consisting of 4-hydroxy-5-sec-butyl-3-nitrobenzenesulfonic acid, 2-hydroxy-3-sec-butyl-5-nitrobenzenesulfonic acid, and mixtures thereof, wherein the total inhibitor concentration is in the range of from about 1 to about 2000 ppm versus the styrene monomer being inhibited.

10. A method for inhibiting and retarding the premature polymerization and the polymer growth of styrene monomer comprising adding to said styrene monomer an effective amount of a combination of (A) at least one first inhibitor that is a sulfonated nitrophenol selected from the group consisting of 4-hydroxy-5-sec-butyl-3-nitrobenzenesulfonic acid, 2-hydroxy-3-sec-butyl-5-nitrobenzenesulfonic acid, and mixtures thereof; and (B) at least one second inhibitor selected from the group consisting of nitroxyl compounds, nitrosoanilines, nitrophenols, amines, and mixtures thereof;

wherein the total inhibitor concentration is in the range of from about 1 to about 2000 ppm versus the styrene monomer being inhibited.

11. The method of claim 10 wherein the amine is selected from the group consisting of N-methyl-2-pyrrolidinone, α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-β-naphthylamine, isopropoxydiphenylamine, aldol-α naphthyl amine, symmetrical di-β-naphthyl-p-phenylenediamine, trimethyl dihydroquinoline, ditolylamines, phenyl-α-naphthylamine, phenyl-β-naphthylamine, diaminophenol, 4-cyclohexylaminophenol, p-aminophenol, o-aminophenol, and 5-amino-2-hydroxytoluene.

12. The method of claim 10 wherein the nitrophenol is selected from the group consisting of 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 4-cyano-2-nitrophenol, 3-iodo-4-cyano-5-nitrophenol, m-nitro-p-cresol, and 2,6-dinitro-p-cresol.

13. The method of claim 10 wherein the nitroxyl compound has the structural formula:

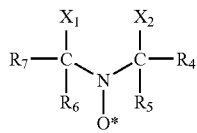

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl; and $X_1$ and $X_2$ (1) are independently selected from the group consisting of halogen, cyano, —COOR10, —S—COR$_{10}$, —OCOR$_{10}$, (wherein $R_{10}$ is alkyl or aryl), amido, —S—C$_6$H$_5$, carbonyl, alkenyl, or alkyl of 1 to 15 carbon atoms, or (2) taken together, form a ring structure with the nitrogen.

14. The method of claim 10 wherein the nitrosoaniline has the structure:

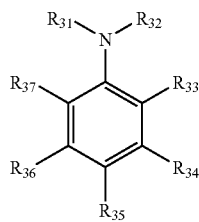

wherein $R_{31}$ and $R_{32}$ are independently selected from the group consisting of hydrogen, alkyl, aryl, acyl, hydroxyl, alkoxy, nitroso, and sulfonyl, or $R_{31}$ and $R_{32}$ can form a cyclic ring that is aryl, cycloalkyl, polyaryl, or heterocyclic;

$R_{33}$ through $R_{37}$ are independently selected from the group consisting of hydrogen, alkyl, aryl, acyl, hydroxyl, alkoxy, acyloxy, NR$_{38}$(R$_{39}$), nitro, nitroso, halogen, and sulfonyl, or any two adjacent R's can form a cyclic ring that is aryl, cycloalkyl, polyaryl, or heterocyclic, provided that at least one of $R_{33}$ through $R_{37}$ must be a nitroso group; and $R_{38}$ and $R_{39}$ are independently selected from the group consisting of hydrogen, alkyl, aryl, acyl, and nitroso.

15. The method of claim 10 wherein the second inhibitor comprises a mixture of 1 to 1000 ppm of at least one nitroxyl compound, 1-500 ppm of at least one amine, and 1 to 1000 ppm of at least one nitrophenol.

16. The method of claim 15 wherein the nitroxyl compound is 4-oxo-2,2,6,6-tetramethyl-1-piperidinyloxy, the amine is N-methyl-pyrrolidinone, and the nitrophenol is 2,4-dinitro-o-sec-butyiphenol.

17. The method of claim 10 wherein the second inhibitor comprises a mixture of 1 to 1000 ppm of at least one nitrosoaniline, 1-500 ppm of at least one amine, and 1 to 1000 ppm of at least one nitrophenol.

18. The method of claim 17 wherein the nitrosoaniline is 4-nitroso-N-(2,4-dimethylpentyl)-aniline, the amine is N-methyl-pyrrolidinone, and the nitrophenol is 2,4-dinitro-o-sec-butylphenol.

* * * * *